US010265129B2

(12) United States Patent
Beira (10) Patent No.: US 10,265,129 B2
(45) Date of Patent: Apr. 23, 2019

(54) MECHANICAL TELEOPERATED DEVICE COMPRISING AN INTERCHANGEABLE DISTAL INSTRUMENT (71) Applicant: DistalMotion SA, Lausanne (CH)

(72) Inventor: Ricardo Daniel Rita Beira, Lausanne (CH)

(73) Assignee: DistalMotion SA, Epalinges (CH)

( * ) Notice: Subject to any disclaimer, the term of this patent is extended or adjusted under 35 U.S.C. 154(b) by 435 days.

(21) Appl. No.: 15/116,509

(22) PCT Filed: Jan. 26, 2015

(86) PCT No.: PCT/EP2015/051473
§ 371 (c)(1),
(2) Date: Aug. 3, 2016

(87) PCT Pub. No.: WO2015/113933
PCT Pub. Date: Aug. 6, 2015

(65) Prior Publication Data
US 2016/0346053 A1    Dec. 1, 2016

(30) Foreign Application Priority Data

Feb. 3, 2014    (CH) .......................... 138/14
Mar. 12, 2014   (EP) .................... 14159025
Mar. 18, 2014   (CH) .......................... 408/14

(51) Int. Cl.
A61B 17/00    (2006.01)
A61B 34/00    (2016.01)
(Continued)

(52) U.S. Cl.
CPC .............. *A61B 34/35* (2016.02); *A61B 34/30* (2016.02); *A61B 34/37* (2016.02); *A61B 34/71* (2016.02);
(Continued)

(58) Field of Classification Search
CPC ................. A61B 34/37; A61B 34/71
See application file for complete search history.

(56) References Cited

U.S. PATENT DOCUMENTS 2,774,488 A    12/1956    Goertz
2,846,084 A    8/1958    Goertz et al.
(Continued)

FOREIGN PATENT DOCUMENTS

CN    101584594 A    11/2009
CN    101637402 A    2/2010
(Continued)

OTHER PUBLICATIONS

Abbott, et al., "Design of an Endoluminal Notes Robotic System," IEEE/RSJ International Conference on Intelligent Robots and Systems, San Diego, CA, pp. 410-416 (2007).
(Continued)

Primary Examiner — Terence Boes
(74) Attorney, Agent, or Firm — Foley & Lardner LLP; Christopher C. Bolten; Nicola A. Pisano (57) ABSTRACT Disclosed is a mechanical teleoperated device comprising i) a handle (30) placed in a proximal part of the device, having a plurality of handle links interconnected by respective handle joints, ii) an end effector (31) placed in a distal part of the device, having a plurality of end-effector links interconnected by respective end-effector joints, iii) a transmission system arranged to kinematically connect the end effector to the handle such that movements of the end effector correspond to movements of the handle, comprising at least one arrangement of a plurality of rotatable elements (41a-d) coaxially mounted together about an axis and arranged to rotate independently from each other, b) first transmission means comprising driving elements (62a-c) which are arranged to actuate in rotation of the plurality of rotatable elements (41a-d) based upon movements of the
(Continued)

handle, c) second transmission means comprising driven elements (63*a*-*c*) which are arranged to be driven by rotation of the plurality of rotatable elements resulting in movement of the end effector links, wherein the transmission system is configured for removably coupling together the first and second transmission means wherein each driven element is removably coupled to one corresponding rotatable element.

15 Claims, 8 Drawing Sheets

(51) Int. Cl.
  *A61B 34/30* (2016.01)
  *A61B 34/35* (2016.01)
  *A61B 34/37* (2016.01)
  *A61B 90/50* (2016.01)
(52) U.S. Cl.
  CPC ............... *A61B 2017/00477* (2013.01); *A61B 2090/506* (2016.02)

(56) References Cited

U.S. PATENT DOCUMENTS

| | | |
|---|---|---|
| 4,756,655 A | 7/1988 | Jameson |
| 5,147,357 A | 9/1992 | Rose et al. |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,951,587 A | 9/1999 | Qureshi et al. |
| 6,026,701 A | 2/2000 | Reboulet |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,554,844 B2 | 4/2003 | Lee et al. |
| 6,786,896 B1 | 9/2004 | Madhani et al. |
| 6,788,999 B2 | 9/2004 | Green |
| 6,850,817 B1 | 2/2005 | Green |
| 6,852,107 B2 | 2/2005 | Wang et al. |
| 6,902,560 B1 | 6/2005 | Morley et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,398,707 B2 | 7/2008 | Morley et al. |
| 7,481,824 B2 | 1/2009 | Boudreaux et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,224,485 B2 | 7/2012 | Unsworth |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,403,832 B2 | 3/2013 | Cunningham et al. |
| 8,418,904 B2 | 4/2013 | Wenchell et al. |
| 8,496,152 B2 | 7/2013 | Viola |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,603,077 B2 | 12/2013 | Cooper et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,696,666 B2 | 4/2014 | Sanai et al. |
| 8,709,000 B2 | 4/2014 | Madhani et al. |
| 8,768,509 B2 | 7/2014 | Unsworth |
| 8,792,688 B2 | 7/2014 | Unsworth |
| 8,801,752 B2 | 8/2014 | Fortier et al. |
| 8,818,560 B2 | 8/2014 | Kishi |
| 8,821,480 B2 | 9/2014 | Burbank |
| 8,828,046 B2 | 9/2014 | Stefanchik et al. |
| 8,845,517 B2 | 9/2014 | Russo |
| 8,845,622 B2 | 9/2014 | Paik et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,861 B2 | 8/2015 | Martin et al. |
| 9,149,339 B2 | 10/2015 | Unsworth |
| 9,307,894 B2 | 4/2016 | Von Grunberg et al. |
| 9,480,531 B2 | 11/2016 | Von Grunberg |
| 9,696,700 B2 | 7/2017 | Beira et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0236316 A1 | 11/2004 | Danitz et al. |

(56) References Cited

U.S. PATENT DOCUMENTS

| | | |
|---|---|---|
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1* | 10/2008 | Coe .................. A61B 17/00234 606/1 |
| 2008/0314181 A1 | 12/2008 | Schena |
| 2009/0036902 A1 | 2/2009 | Dimaio et al. |
| 2009/0198253 A1 | 8/2009 | Omori |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0299141 A1 | 12/2009 | Downey et al. |
| 2010/0004508 A1 | 1/2010 | Naito et al. |
| 2010/0023025 A1 | 1/2010 | Zeiner et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2011/0087236 A1 | 4/2011 | Stokes et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0027762 A1 | 2/2012 | Schofield |
| 2012/0031114 A1 | 2/2012 | Mueller et al. |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0209292 A1 | 8/2012 | Devengenzo et al. |
| 2012/0253326 A1 | 10/2012 | Kleyman |
| 2012/0277762 A1 | 11/2012 | Lathrop et al. |
| 2012/0289973 A1* | 11/2012 | Prisco .................. A61B 34/30 606/130 |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0304083 A1 | 11/2013 | Kaercher et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grünberg |
| 2014/0188091 A1 | 7/2014 | Vidal et al. |
| 2014/0188159 A1 | 7/2014 | Steege |
| 2014/0200561 A1 | 7/2014 | Ingmanson et al. |
| 2014/0207150 A1 | 7/2014 | Rosa et al. |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0142018 A1 | 5/2015 | Sniffin et al. |
| 2015/0150575 A1 | 6/2015 | Hartoumbekis et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0374766 A1 | 12/2016 | Schuh |
| 2017/0273749 A1* | 9/2017 | Grover .................. A61B 34/30 |
| 2018/0055583 A1* | 3/2018 | Schuh .................. A61B 34/30 |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |

(56) References Cited

FOREIGN PATENT DOCUMENTS

| | | |
|---|---|---|
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2012/020386 A1 | 2/2012 |
| WO | WO-2012/049623 A1 | 4/2012 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2016/083189 A1 | 6/2016 |
| WO | WO-01/6189284 A1 | 12/2016 |
| WO | WO-2016/189284 A1 | 12/2016 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |

OTHER PUBLICATIONS

Aesculap Surgical Technologies, Aesculap® Caiman®, Advanced Bipolar Seal and Cut Technology Brochure, 6 pages (retrieved Aug. 31, 2015).

Arata, et al., "Development of a dexterous minimally-invasive surgical system with augmented force feedback capability," IEEE/RSJ International Conference on Intelligent Robots and Systems, pp. 3207-3212 (2005).

çavuŞ oğlu, et al., "Laparoscopic Telesurgical Workstation," IEEE Transactions on Robotics and Automation,(15)4:728-739 (1999).

Dachs, et al., "Novel Surgical Robot Design: Minimizing the Operating Envelope Within the Sterile Field," 28th International Conference, IEEE Engineering in Medicine Biology Society, New York, pp. 1505-1508 (2006).

Dario, et al., "Novel Mechatronic Tool for Computer-Assisted Arthroscopy," IEEE Transactions on Information Technology in Biomedicine, 4(1):15-29 (Mar. 2000).

Focacci, et al., "Lightweight Hand-held Robot for Laparoscopic Surgery," IEEE International Conference on Robotics & Automation, Rome, Italy, pp. 599-604 (2007).

Guthart, et al., "The Intuitive™ Telesurgery System: Overview and Application," IEEE International Conference on Robotics & Automation, San Francisco, CA, pp. 618-621 (2000).

Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).

Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).

International Search Report & Written Opinion dated Feb. 2, 2017 in Int'l PCT Patent Appl. Serial No. PCT/IB2016/001286.

International Search Report & Written Opinion dated Jan. 18, 2013 in Int'l PCT Patent Appl Serial No. PCT/IB2012/053786.

International Search Report dated Jan. 18, 2013 in Int'l PCT Patent Appl Serial No. PCT/IB2012/053786.

International Search Report dated Mar. 23, 2012 in Int'l PCT Patent Appl Serial No. PCT/IB2011/054476.

Ishii, et al., "Development of a New Bending Mechanism and Its Application to Robotic Forceps Manipulator," IEEE International Conference on Robotics & Automation, Rome, Italy, pp. 238-243 (2007).

International Search Report & Written Opinion dated May 23, 2016 in Int'l PCT Patent Appl Serial No. PCT/IB2015/002524.

International Search Report & Written Opinion dated Mar. 30, 2015 in Int'l PCT Patent Appl Serial No. PCT/EP2015/051473.

International Search Report & Written Opinion dated Apr. 26, 2016 in Int'l PCT Patent Appl Serial No. PCT/IB2015/002512.

International Search Report & Written Opinion dated May 24, 2016 in Int'l PCT Patent Appl Serial No. PCT/IB2015/002487.

International Search Report & Written Opinion dated Jun. 10, 2016 in Int'l PCT Patent Appl Serial No. PCT/IB2015/002533.

International Search Report & Written Opinion dated Jun. 13, 2016 in Int'l PCT Patent Appl Serial No. PCT/IB2015/002493.

International Search Report & Written Opinion dated Aug. 25, 2016 in Int'l PCT Patent Appl Serial No. PCT/IB2016/000542.

International Search Report & Written Opinion dated Sep. 2, 2016 in Int'l PCT Patent Appl Serial No. PCT/IB2016/000543.

Kobayashi, et al., "Small Occupancy Robotic Mechanisms for Endoscopic Surgery," International Conference on Medical Image Computing and Computer assisted Interventions, pp. 75-82 (2002).

Mayer, et al., "The Endo[PA]R System for Minimally Invasive Robotic Surgery," IEEE/RSJ International Conference on Intelligent Robots and Systems, Sendai, Japan, pp. 3637-3642 (2004).

Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).

Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).

Peirs, et al., "Design of an advanced tool guiding system for robotic surgery," IEEE International Conference on Robotics & Automation, Taipei, Taiwan, pp. 2651-2656 (2003).

Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).

Seibold, et al., "Prototype of Instrument for Minimally Invasive Surgery with 6-Axis Force Sensing Capability," IEEE International Conference on Robotics & Automation, Barcelona, Spain, pp. 496-501 (2005).

Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).

Stryker®, Endoscopy, Take a Look Around, Ideal Eyes™ FFD122 HD, Articulating Laparoscope Brochure, 2 pages (2009).

Swiss Search Report dated Jun. 4, 2012 in Swiss Patent Application No. CH 00702/12.

Tavakoli, et al., "Force Reflective Master-Slave System for Minimally Invasive Surgery," IEEE/RSJ International Conference on Intelligent Robots and Systems, Las Vegas, NV, pp. 3077-3082 (2003).

Taylor, et al., "Steady-Hand Robotic System for Microsurgical Augmentation," The International Journal of Robotics Research, 18(12):1201-1210 (1999).

www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.

Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages (2005).

(56) References Cited

OTHER PUBLICATIONS

Zeus, "Robotic Surgical System" available at http://al-laboutroboticsurgery.com/zeusrobot.html.

* cited by examiner

MECHANICAL TELEOPERATED DEVICE COMPRISING AN INTERCHANGEABLE DISTAL INSTRUMENT

CROSS-REFERENCE TO RELATED APPLICATIONS

This application is a national phase of International PCT Patent Application No. PCT/EP2015/051473, filed Jan. 26, 2015, which claims priority to Switzerland Patent Application No. CH00408/14, filed Mar. 18, 2014, EPO Patent Application No. 14159025.7, filed Mar. 12, 2014, and Switzerland Patent Application No. CH00138/14, filed Feb. 3, 2014, the entire contents of each of which are incorporated herein by reference.

FIELD OF THE INVENTION

The present invention relates to the field of remotely actuated mechanical systems. In particular embodiments, the invention relates to a mechanical teleoperated device for use primarily in surgical procedures and comprising an interchangeable distal instrument. Certain embodiments have particular applicability in minimally invasive surgical procedures. The present invention is also suitable for any remotely actuated application requiring dexterous manipulation with high stiffness and precision along with force feedback. Examples of such applications include assembly manipulation, manipulation in narrow places, manipulation in dangerous or difficult environments, and manipulation in contaminated or clean-room environments.

BACKGROUND OF THE INVENTION

Numerous environments and applications call for remote actuation with mechanically teleoperated devices. These applications include fine manipulation in assembly tasks, manipulation in narrow places, manipulation in dangerous or contaminated environments, manipulation in clean-room or sterile environments and manipulation in surgical environments, whether open field or minimally invasive. While these applications vary along parameters such as precise tolerances and typical end user, each demands many of the same features from a mechanically teleoperated system, such as the ability to carry out dexterous manipulation with high stiffness and precision along with force feedback.

Surgical applications are now discussed in more detail as a representative example of an application for a mechanically teleoperated device system where known devices exist but significant shortcomings are evident in the current state of the art.

Open surgery is still the standard technique for most surgical procedures. It has been used by the medical community for several decades and consists of performing the surgical tasks by making a long incision in the abdomen or other area of the body, through which traditional surgical tools are inserted. However, due to the long incision, this approach is extremely invasive for patients, resulting in substantial blood loss during surgery and, typically, long and painful recovery periods in a hospital setting.

In order to reduce the invasiveness of open surgery, laparoscopy, a minimally invasive technique, was developed. Instead of a single long incision, several small incisions are made in the patient through which long and thin surgical instruments and endoscopic cameras are inserted. Because of the minimally invasive nature of the procedure, this technique reduces blood loss and pain and shortens hospital stays. When performed by experienced surgeons, this technique can attain clinical outcomes similar to open surgery. However, despite the above-mentioned advantages, laparoscopy requires extremely advanced surgical skill to manipulate the rigid and long instrumentation. The entry incision acts as a point of rotation, decreasing the freedom for positioning and orientating the instruments inside the patient. The movements of the surgeon's hand about this incision are inverted and scaled-up relative to the instrument tip ("fulcrum effect"), which reduces dexterity and sensitivity and magnifies the tremors of the surgeon hands. In addition, the long and straight instruments force the surgeon to work in an uncomfortable posture for hands, arms and body, which can be tremendously tiring during several hours of an operation. Therefore, due to these drawbacks of laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of remote laparoscopy where the surgeon sits at a console manipulating two master manipulators to perform the operation through several small incisions. Like laparoscopy, the robotic approach is also minimally invasive, bringing the above-mentioned advantages over open surgery in terms of pain, blood loss, and recovery time. In addition, it also offers better ergonomy for the surgeon compared to open and laparoscopic techniques. However, although being technically easier, robotic surgery brings several negative aspects. A major disadvantage of these systems relates to the extremely high complexity of the existing robotic devices, which comprise complex mechatronic systems, leading to huge costs of acquisition and maintenance, which are not affordable for the majority of surgical departments worldwide. Another drawback of these systems comes from the fact that current surgical robots are large, competing for precious space within the operating room environment and significantly increasing preparation time. Access to the patient is thus impaired, which, together with a general lack of force-feedback, raises safety concerns.

WO9743942, WO9825666 and U.S.2010011900 disclose a robotic tele-operated surgical instrument, designed to replicate surgeons' hand movements inside the patient's body. By means of a computerized, robotic interface, it enables the performance of remote laparoscopy, wherein the surgeon sits at a console manipulating two joysticks to perform the operation through several small incisions. However, this system does not have autonomy or artificial intelligence, being essentially a sophisticated tool fully controlled by the surgeon. The control commands are transmitted between the robotic master and robotic slave by a complex computer-controlled mechatronic system, which is extremely costly to produce and maintain and difficult to use for the hospital staff.

WO2012049623 describes a mechanical manipulator for surgical instruments with a master-slave configuration and including remote actuation of a distal end effector. However, the system described therein does not provide for an interchangeable instrument.

WO2013014621 describes a mechanical teleoperated device for remote manipulation which comprises master-slave configuration including a slave unit driven by a kinematically equivalent master unit such that each part of the slave unit mimics the movement of each corresponding part of the master unit. Although the mechanical transmission system is well adapted to the device, cables passing through an axial joint are twisted when the device is operating, which can force the cables to rub against each other. This increases wear on the cables over time and increases friction in the overall mechanical transmission.

Accordingly, an aim of the present invention is to provide a mechanical teleoperated device comprising an interchangeable distal instrument. This device could be designed for use in a surgical environment such that the interchangeable distal instruments would be surgical instruments. However, one of skill in the art will realize that the device could also be deployed in other applications where complex, remote manipulation is required and wherein interchangeable instruments would be useful for different manipulation tasks.

Another aim of the present invention is to provide a mechanical teleoperated system with an improved transmission system. In such a system, the transmission system, and particularly the joints, would be designed such that cables do not rub against each other, thus reducing wear and tear.

SUMMARY OF THE INVENTION

These aims and other advantages are achieved through a mechanical teleoperated device for remote manipulation designed to naturally replicate the operator's hand movements in the distal area where the manipulation must occur. The mechanical teleoperated device may comprise a slave unit, configured to be driven by a master unit, which is preferably kinematically equivalent to the slave unit. The slave unit has a plurality of slave links interconnected by respective slave joints and comprises a proximal part and a distal part (also referred to as a distal instrument) connected distally to one of the slave joints, referred to as the interface slave joint. More particularly, this interface slave joint of the slave unit may have a coaxial configuration, connecting a proximal and a distal link of the slave unit in such a manner that these two adjoining links are axially rotatable with respect to each other about the axis of the coaxial joint. The master unit comprises a plurality of master links interconnected by respective master joints, and a corresponding interface master joint.

An articulated handle is connected to the master unit for operating the mechanical teleoperated device and an articulated end-effector is connected to the distal extremity of the distal instrument. The mechanical teleoperated device further comprises a transmission system arranged to kinematically connect the equivalent degrees-of-freedom of the master and slave units, including the degrees-of-freedom of the end-effector to the degrees-of-freedom of the handle such that said end-effector replicates the movements of the handle when the mechanical teleoperated device is operated.

The transmission system comprises (i) at least one arrangement of a plurality of rotatable elements coaxially mounted together and coaxial to the axis of the interface slave joint of the slave unit and arranged to rotate independently from each other; (ii) first transmission means integrated into the proximal part of the slave unit and comprising driving cables or the like which are arranged to actuate in rotation each one of the rotatable elements of the said at least one arrangement; and (iii) second transmission means integrated into the distal instrument and comprising driven cables or the like which are arranged to be driven by the rotation of each one of the corresponding rotatable elements of the at least one arrangement of a plurality of rotatable elements.

The transmission system according to the invention is advantageously configured for removably coupling together the first and second transmission means of the respective proximal and distal parts of the slave unit. In this arrangement, each driven cable of said second transmission means is removably connected, by means of additional elements, to one corresponding rotatable element of said at least one arrangement of a plurality of rotatable elements in order to provide a user-friendly interchangeable and modular tooling/instrument system for use with the mechanical teleoperated device.

According to one embodiment of the invention, a segment of each driven cable of the second transmission means is removably connected to one corresponding rotatable element of the at least one arrangement of a plurality of rotatable elements. Each of these segments is guided along a path within a plane which is substantially perpendicular to the axis about which the rotatable elements of the at least one arrangement of a plurality of rotatable elements are able to rotate. This path preferably extends along a circular trajectory, whose center point is coincident with the rotatable elements' axis.

According to another embodiment of the invention, each driven cable of said second transmission means is anchored to a mating receptacle pivotally mounted about the axis of the interface slave joint of the slave unit. Each corresponding rotatable element of the at least one arrangement of a plurality of rotatable elements comprises a complementary mating part removably mounted inside the corresponding mating receptacle.

According to a further embodiment of the invention, each complementary mating part is mounted on a pointer which is connected to one corresponding rotatable element. These pointers are able to rotate around the axis of the interface slave joint and may be angularly offset from each other so that their angular amplitude of movement allows the full-range actuation of the end-effector articulations.

According to a further embodiment of the invention, the mating receptacles and corresponding mating parts are housed inside a slave housing. The slave housing comprises two complementary housing parts removably mounted against each other. Said mating receptacles are mounted inside one complementary housing part which is connected to the distal part of the slave unit whereas said complementary mating parts are mounted inside the other complementary housing part which is connected to the proximal part of the slave unit.

According to another embodiment of the invention, the transmission system comprises two arrangements of a plurality of rotatable elements, wherein rotatable elements of the first arrangement are coaxially mounted together so that each one is able to rotate about the axis of an interface slave joint of the slave unit, and wherein rotatable elements of the second arrangement are coaxially mounted together to rotate about each other, being collinear with the axis of an interface master joint of the master unit. In this configuration, each driving cable of the first transmission means is connected to one rotatable element of the first arrangement of the slave unit and to one corresponding rotatable element of the second arrangement of the master unit such that rotation of each rotatable element of said second arrangement rotates the corresponding rotatable element of said first arrangement.

According to yet another embodiment of the invention, two or more teleoperated devices, as defined above, can be set to work together, enabling the user to perform bi-manual manipulation. In addition, two or more telemanipulators can be mounted on a movable and articulated station, so that they can be easily moved on the ground from one place to the other and their working position and orientation can be tuned in the 3D space.

BRIEF DESCRIPTION OF THE FIGURES

The invention will be better understood according to the following detailed description of several embodiments of the invention with reference to the attached figures, in which.

DETAILED DESCRIPTION OF THE INVENTION

Figure 3:
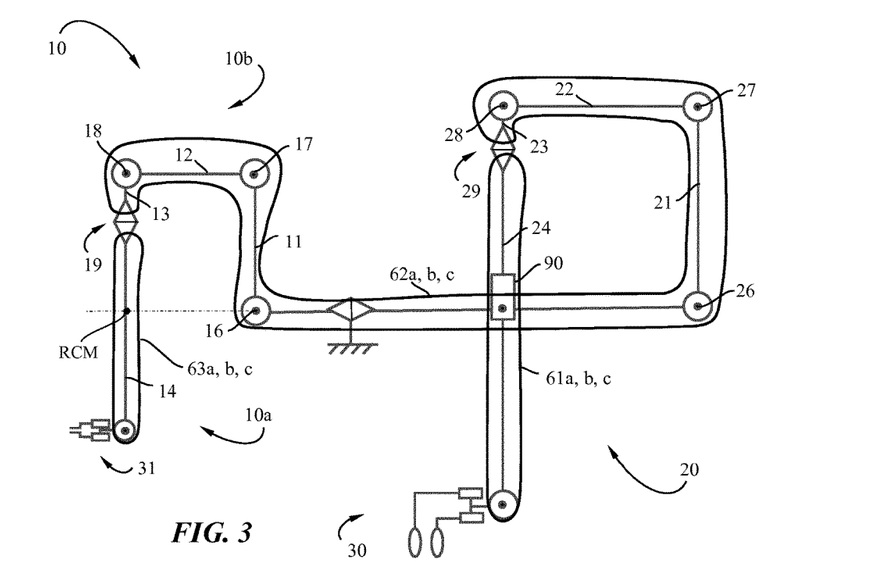
FIG. 3 shows a schematic view of the transmission system of FIG. 1 comprising first, second and third transmission means.
Figure 12:
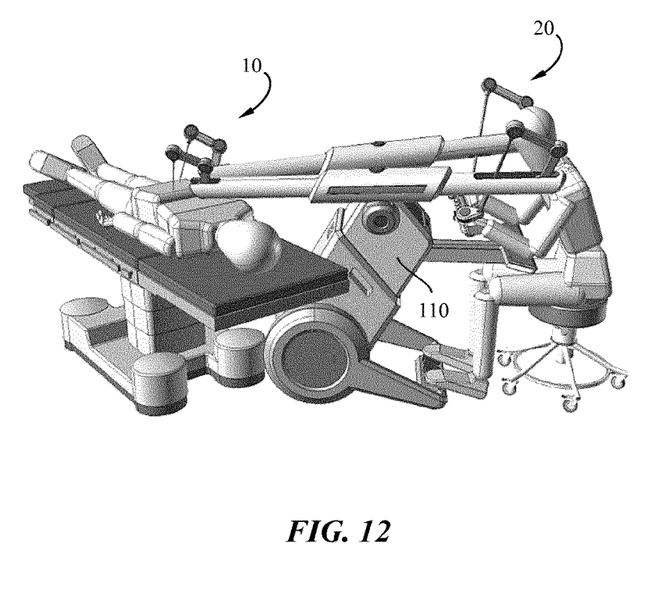
FIG. 12 shows an exemplary embodiment comprising two identical mechanical teleoperated devices of FIG. 1 mounted on an articulated and movable station, namely a mechanical telemanipulator for surgical procedures.

A mechanical telemanipulator, which may be used in minimally invasive surgical procedures or in other applications, constructed in accordance with an embodiment of the present invention, is described herein, and is seen generally in FIG. 12. This manipulator comprises preferably two identical mechanical teleoperated devices, as shown for example in FIG. 1, mounted on an articulated and movable station 110 (FIG. 12) and configured to be operated independently from the other. Each mechanical teleoperated device of FIG. 1, as conceptually described in WO2013/014621, comprises, on the one hand, a master-slave configuration, having a slave unit 10 driven by a kinematically equivalent master unit 20 and, on the other hand, mechanical constraint means 90 such that each part of the slave unit 10 mimics the movement of each corresponding part of the master unit 20 without deviating, during operation of the device, from a remote-center-of-motion (RCM) as shown in FIG. 3. However, in other embodiments of the current invention, the mechanical teleoperated device may not have a remote-center-of-motion (RCM). Given that the two mechanical teleoperated devices are structurally and functionally identical, the description hereafter will refer to one mechanical teleoperated device only as shown particularly in FIGS. 1 to 6.

Referring more particularly to FIG. 3, the slave unit 10 comprises a plurality of slave links 11, 12, 13, 14 interconnected by respective slave joints 16, 17, 18, 19. An articulated end-effector 31 is mounted at the distal end of the slave link 14 which is rotatably connected to the adjoining link 13 through an coaxial joint 19 such that the two adjoining links 13, 14 are coaxially rotatable with respect to each other about the axis of the axial joint 19. The remaining slave joints 16, 17, 18 of the slave unit 10 are of the type of so-called pivot-joint which connects two adjoining links (e.g. pivot joint 17 connecting link 12 with link 13) in order to be angularly actuable with respect to each other within a plane perpendicular to the axis of rotation of said pivot-joint. The master unit 20 comprises a structural and kinematic configuration identical to the slave unit 10. More particularly, the master unit 20 comprises a corresponding plurality of master links 21, 22, 23, 24 interconnected by respective master joints 26, 27, 28, 29. One of these joints is a coaxial joint 29 while the other joints are pivot-joints 26, 27, 28. An articulated handle 30 is connected at the distal end of a master link 24 of the master unit 20 for operating the mechanical teleoperated device.

Upward and downward movements applied to the handle 30 by the operator when the mechanical teleoperated device is in the neutral position of FIG. 3 translate the master link 24 along its longitudinal axis through the mechanical constraint means 90 whereas frontward and backward movements applied on the handle rotate the master link 24 about an axis parallel to the axis of each pivot-joint. Each one of these movements or a combination thereof generates angular displacement of the master joints 26, 27, 28, 29 of the master unit 20 wherein said angular displacement of each master joint causes, through mechanical transmission, an identical angular displacement of the corresponding slave joint 16, 17, 18, 19 of the slave unit 10. The kinematic connection between each pivot-joint 26, 27, 28 of the master unit 20 with the corresponding pivot joint 16, 17, 18 of the slave unit 10, is achieved by pulley-routed cables which are each arranged to be anchored to two corresponding pulleys rotatably mounted around a shaft whose axis is coincident with the axis the corresponding pivot-joint. Kinematic connections between each pivot-joint 16, 17, 18 of the slave unit 10 with the corresponding pivot-joint 26, 27, 28 of the master unit 20 are described in more details in the aforementioned PCT application (WO2013/014621). In this configuration, the kinematic model of the chain formed by the plurality of slave links 11, 12, 13, 14 and respective slave joints 16, 17, 18, 19 of the slave unit 10 is identical to the kinematic model of the chain formed by the plurality of master links 21, 22, 23, 24 and respective master joints 26, 27, 28, 29 of the mater unit 20.

Figure 2:
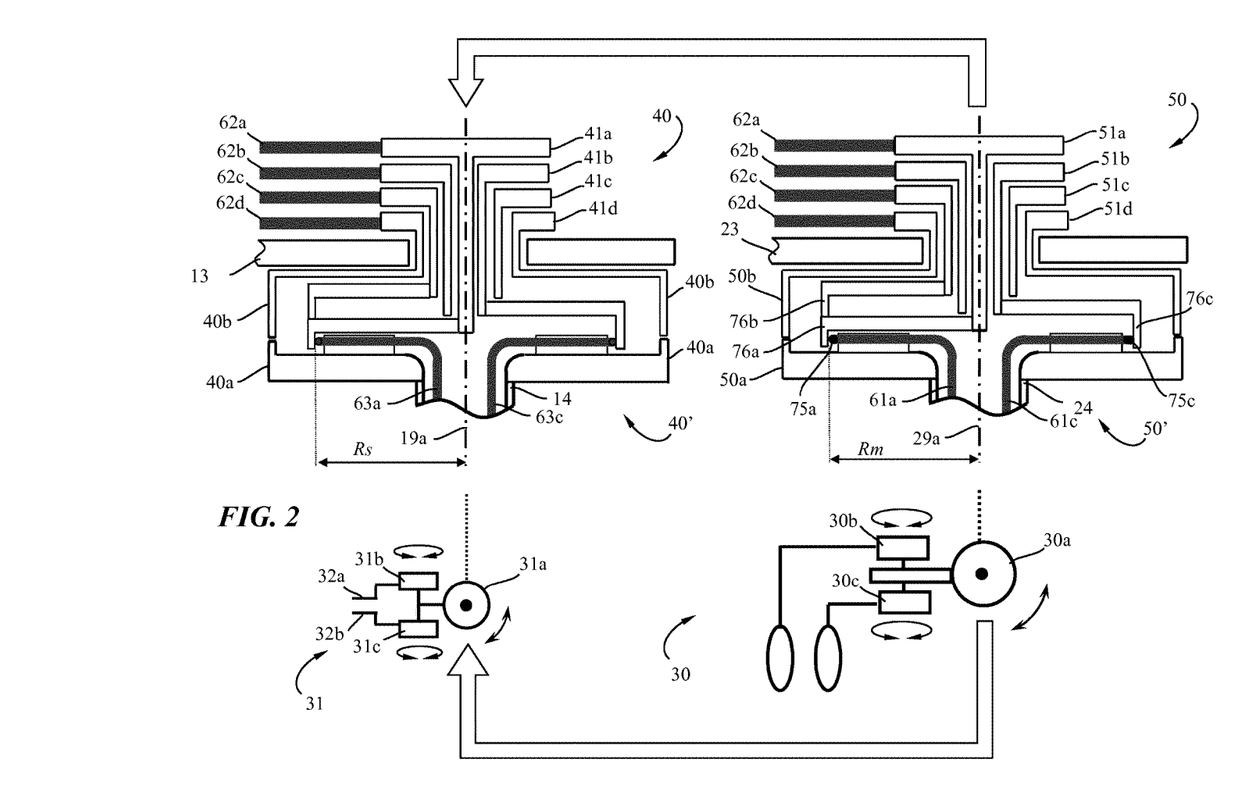
FIG. 2 shows a schematic view of the transmission system of the mechanical teleoperated device of FIG. 1.

As schematically shown in FIG. 2, the handle 30 is configured to actuate three degrees-of-freedom of the end effector 31 by a transmission system adapted to kinematically connect three pulleys 30a, 30b, 30c of the handle 30 with three corresponding pulley 31a, 31b, 31c of the end-effector 31. In this way, angular displacement of each pulley of the handle 30, when the teleoperated surgical device is operating, is replicated by the corresponding pulley of the end-effector 31. The latter is configured such that counter-rotation of both pulleys 31b, 31c in one direction rotates jaws 32a, 32b in opposite direction away from each other to open the grip of the jaws while counter-rotation of both pulleys 31b, 31c in the other direction rotates the jaws 32a, 32b in opposite directions toward each other to close the grip and maintain a gripping force of the jaws. The working tips of the jaws 32a, 32b have a surface for gripping and may be used, for example, in forceps or cautery applications. Alternately, "gripping" which closes the jaws may be a cutting action when the tips of the jaws 32a, 32b are blades that cooperatively cut as a scissors. Gripping can thus perform different functions depending the nature of the end-effector 31. This end-effector is further configured to pivot about the axis of its pulley 31a when the latter is actuated by the cable-driven system according to the invention.

Figure 1:
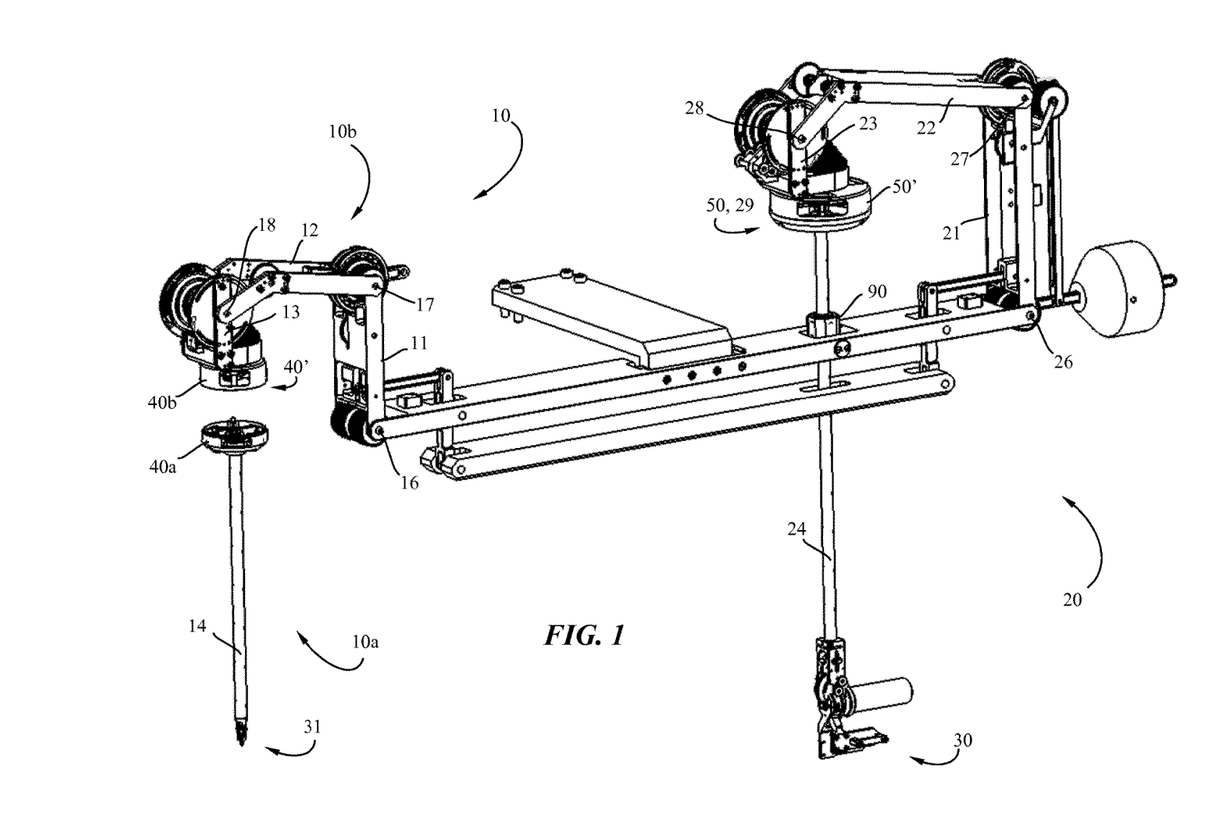
FIG. 1 shows a perspective view of a mechanical teleoperated device according to the invention.

Still referring to FIG. 2, the transmission system according to this preferred embodiment comprises a first arrangement 40 of three rotatable elements 41a, 41b, 41c coaxially mounted together about the axis 19a of the interface slave joint of the slave unit and a second arrangement 50 of three rotatable elements 51a, 51b, 51c coaxially mounted together about the axis 29a of the interface master joint of the master unit. The rotatable element 41d comprises the driven pulley that actuates the interface slave joint 19 of the slave unit 10, being rigidly attached to the slave link 14. The rotatable element 51d comprises the driving pulley that actuates the interface master joint 29 of the master unit 20, being rigidly attached to the master link 24. Rotatable elements 41a, 41b, 41c of the first arrangement 40 are partly housed inside a slave housing 40' while rotatable elements 51a, 51b, 51c of the second arrangement 50 are partly housed inside a master housing 50'. As shown in FIG. 1, the slave and master housings 40', 50' are connected respectively to a distal link 14 of the slave unit 10 and to a corresponding master link 24 of the master unit 20. The slave housing 40' is further connected to the rotatable element 41d whereas the master housing 50' is further connected to the corresponding rotatable element 51d.

The transmission system as shown in FIG. 2 further comprises first transmission means which have three cables 62a, 62b, 62c or similar structure which are each arranged to connect one rotatable element 51a, 51b, 51c of the second arrangement with one corresponding rotatable element 41a, 41b, 41c of first arrangement 40 such that rotation of each rotatable element 51a, 51b, 51c of second arrangement 50 actuates the corresponding cable which rotates in turn the equivalent rotatable element 41a, 41b, 41c of first arrangement 40.

Figure 4:
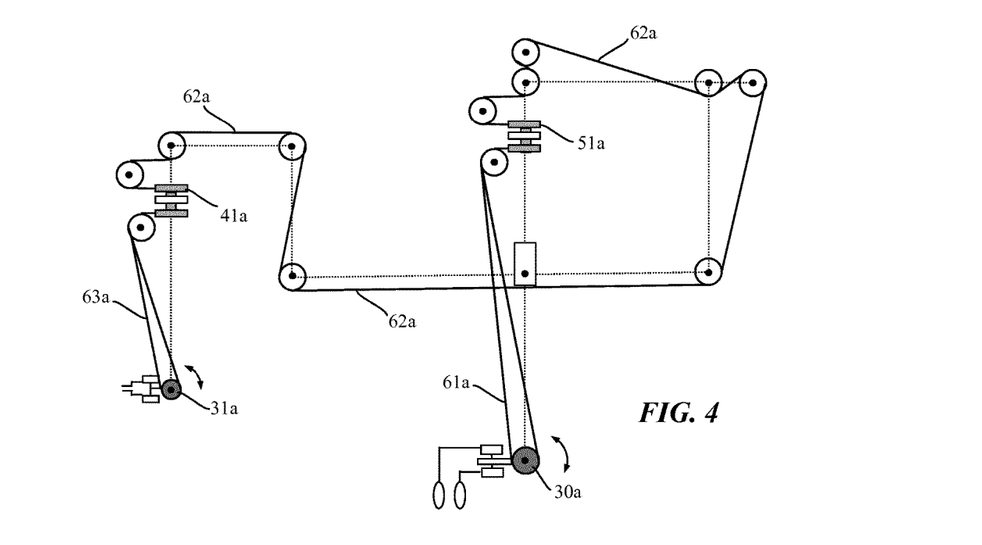
FIGS. 4, 5 and 6 show a schematic view of the transmission system for the transmission of each degree-of-freedom of the handle to the end-effector.
Figure 5:
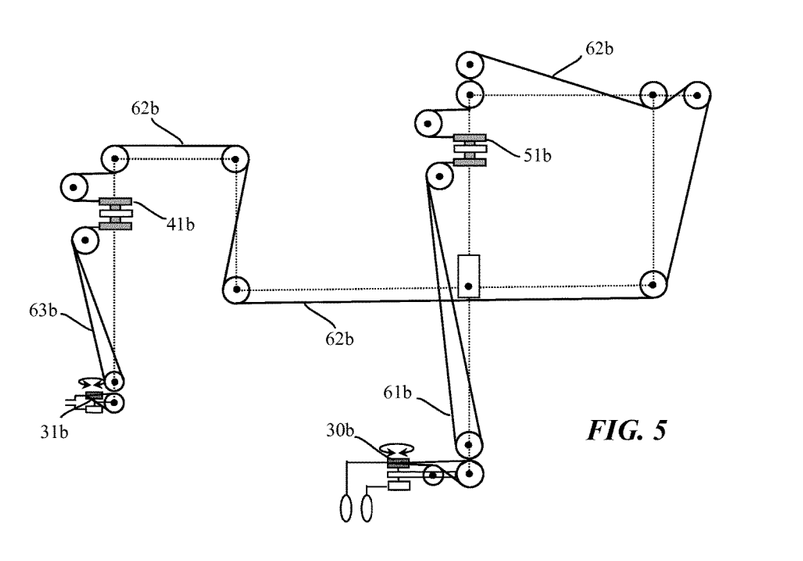
Figure 6:
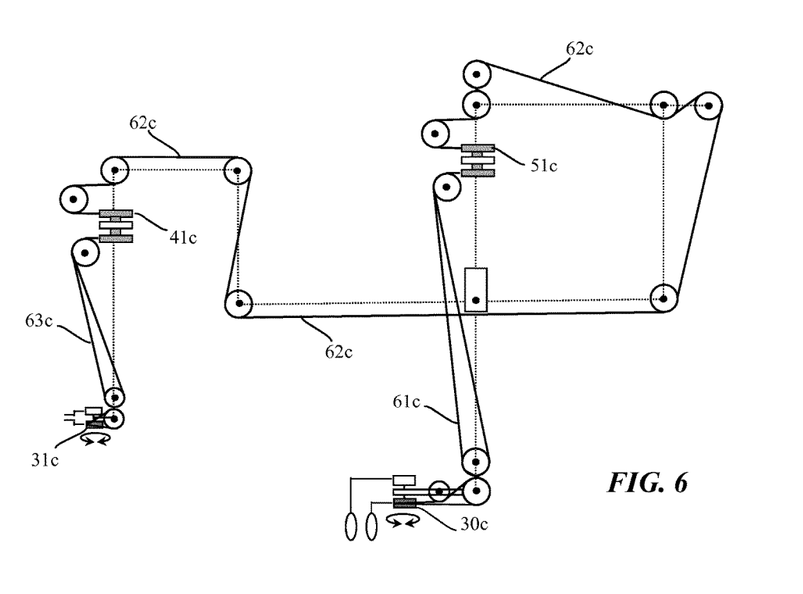

Referring now to FIGS. 4 to 6, the transmission system comprises second transmission means which have three driven cables 63a, 63b, 63c or similar structures which are each arranged to be anchored on a corresponding pulley 31a, 31b, 31c of the end-effector 31 to enable angular displacement of these pulleys about their respective pivotal connection. These driven cables extends axially through the slave link 14 to be removably anchored to a corresponding rotatable element 41a, 41b, 41c of the first arrangement 40 of the slave unit 10. The removable connection of each driven cable to the corresponding rotatable element will be described in details subsequently.

The transmission system further comprises third transmission means which have three cables 61a, 61b, 61c or similar structures which are each arranged to be anchored on a corresponding pulley 30a, 30b, 30c of the handle 30 in order to be driven by angular displacement of these pulleys about their respective pivotal connection generated by the actuation of handle 30. Each of these cables 61a, 61b, 61c extends axially along the master link 24 to be anchored to a corresponding rotatable element 51a, 51b, 51c of the second arrangement 50 of the master unit 20. FIG. 2 partly shows in more details how this type of connection is achieved. Each cable 61a, 61b, 61c (only cables 61a and 61c are visible) are partially guided within a plane which is preferably perpendicular to the axis of the axial joint 29 of the master unit 20 and along a substantially circular path through an angle of less than 120 degrees (on the current embodiment). A segment 75a, 75c (75b is not visible in FIG. 2) of each cables is attached to a corresponding pointer 76a, 76b, 76c, wherein these pointers are coaxially mounted jointly with respective rotatable element 51a, 51b, 51c, and are superposed and angularly offset from each other.

According to the configuration of the transmission system, angular displacement of each pulley 30a, 30b, 30c of the handle 30 about their respective pivotal connection, during operation of the mechanical teleoperated device, drives the corresponding cable 61a, 61b, 61c of the third transmission means which causes the angular displacement of the corresponding rotatable element 51a, 51b, 51c of the second arrangement 50 about the axis of the interface slave joint 29 of the master unit 20. Rotation of each one of these rotatable elements 51a, 51b, 51c drives the corresponding cable 62a, 62b, 62c of the first transmission means which causes the angular displacement of the equivalent rotatable element 41a, 41b, 41c of the first arrangement 40 about the axis of the interface slave joint 19 of the slave unit 10. Rotation of each one of these rotatable elements 41a, 41b, 41c causes in turn the angular displacement of the corresponding pulley 31a, 31b, 31c of the end-effector 31 by means of the corresponding driven cable 63a, 63b, 63c of the second transmission means. The remaining two rotatable elements 41d, 51d of respective slave and master units 10, 20 are connected together by means of cable 62d such that axial rotation of the master link 24 rotates the corresponding slave link 14 about its longitudinal axis.

Due to this particular configuration, the transmission system is advantageously arranged to avoid twisting of the cables, when the master link 24 and the corresponding slave link 14 are coaxially rotating. Wear and tear of the cables resulting from prolonged use of the mechanical teleoperated device are therefore significantly reduced.

Figure 7:
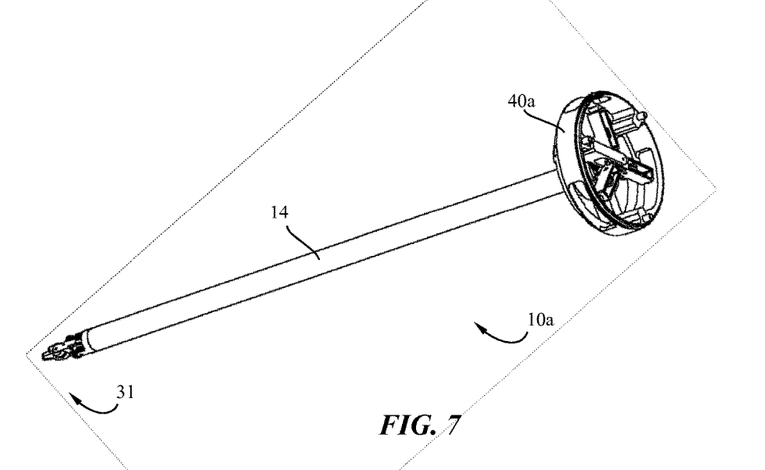
FIG. 7 shows a perspective view of a detachable distal instrument.
Figure 8:
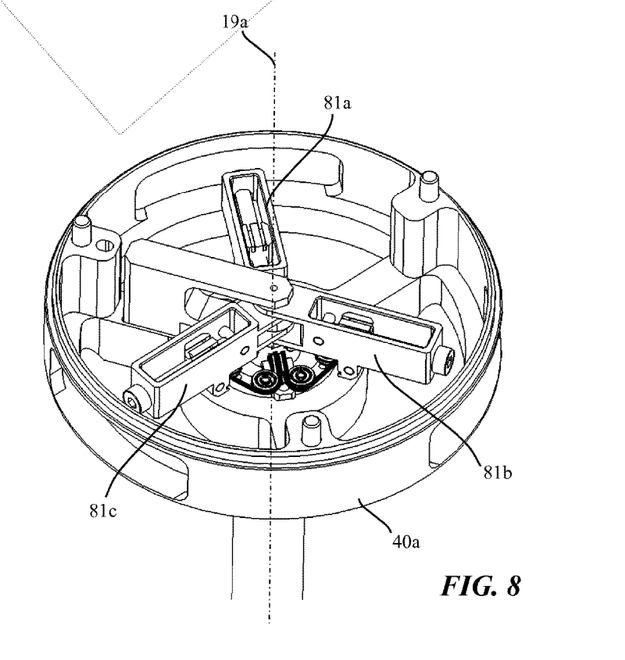
FIG. 8 shows a perspective view of a lower part of the slave housing of the first arrangement of the transmission system containing mating receptacles.
Figure 9:
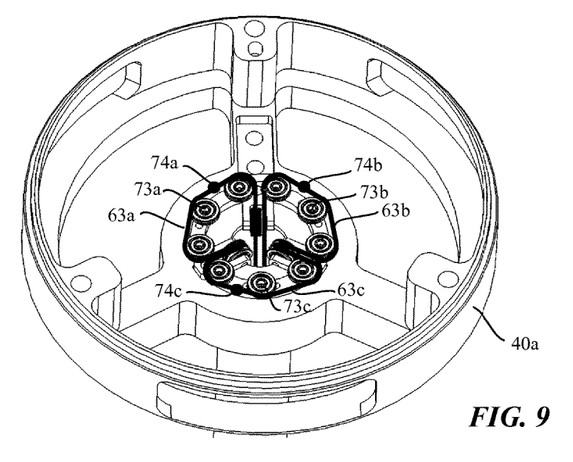
FIG. 9 shows a perspective view of the guiding means of the slave housing of FIG. 8.
Figure 10:
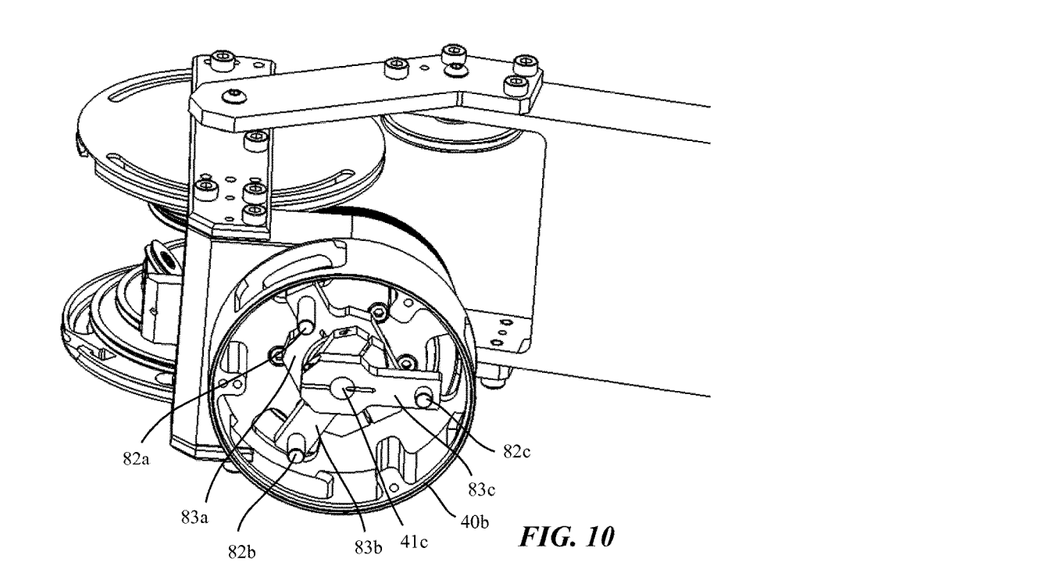
FIG. 10 shows an upper part of the slave housing containing complementary mating parts arranged to be removably mounted inside the corresponding mating receptacle of FIG. 8.

Referring now to FIGS. 8, 9 and 10, the transmission system according to the invention comprises a coupling/decoupling mechanism for removably connecting each driven cable 63a, 63b, 63c of the second transmission means with the corresponding cable 62a, 62b, 62c of the first transmission means in order to provide a user-friendly interchangeable and modular tooling system to the mechanical teleoperated device. To this end, lower and upper parts 40a, 40b of the slave housing 40' are removably secured against each other preferably by means of screws to allow the user to structurally disconnect the distal part 10a (FIG. 7) from the proximal part 10b of the slave unit 10 as particularly shown in FIG. 1.

Figure 11A:
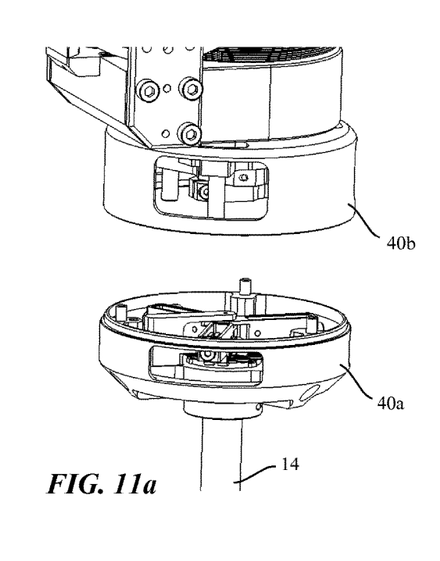
FIGS. 11a, 11b and 11c show three different views of the distal part coupling with the proximal part of the slave unit of the mechanical teleoperated device of FIG. 1.
Figure 11B:
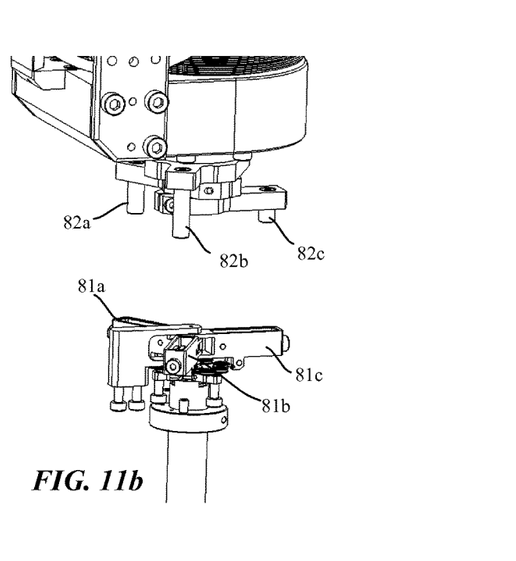
Figure 11C:
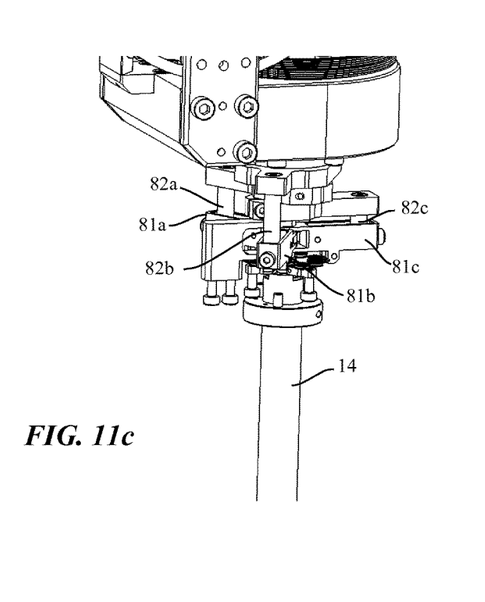

With reference to FIG. 9, the coupling/decoupling device of the transmission system comprises guiding means 73a, 73b, 73c within the lower part 40a of the slave housing. Each of these guiding means 73a, 73b, 73c are preferably in the form of a series of rollers arranged to guide a segment 74a, 74b, 74c of each cable 63a, 63b, 63c of the second transmission means within a plane which is substantially perpendicular to the axis of the interface slave joint 19 of the slave unit 10 and along a substantially circular path through a certain angular range. In other embodiments of the same invention, instead of being composed by a series of rollers, the guiding means may comprise non-moving elements or surfaces in order to guide the segment 74a, 74b, 74c of each cable 63a, 63b, 63c of the second transmission means within their path. Each segment 74a, 74b, 74c of each one of these cables is anchored to a mating receptacle 81a, 81b, 81c pivotally mounted about the axis 19a of said interface slave joint 19 of the slave unit 10 as shown in FIG. 8. As can be seen in FIG. 10, a complementary mating part 82a, 82b, 82c, preferably in the form of a connecting pin, is mounted on respective supports 83a, 83b, 83c which are coaxially arranged jointly with respective rotatable element of the first arrangement. These supports 83a, 83b, 83c which are preferably in the form of pointers are superposed and angularly offset from each other. Each connecting pin 82a, 82b, 82c is adapted to be removably mounted inside the corresponding mating receptacle 81a, 81b, 81c as particularly shown in FIG. 11c.

According to the transmission system, the ratio of Rs/Rm (FIG. 2) equates to the ratio of Ds/Dm wherein:
 i) Rs is the radial distance between the axis of the interface slave joint 19 of the slave unit 10 and one anchored segment 73a, 73b, 73c of one driven cable 63a, 63b, 63c of the second transmission means;
 ii) Rm is the radial distance between the axis of the interface slave joint 29 of the master unit 20 and one anchored segment of one cable 61a, 61b, 61c of the third transmission means;
 iii) Ds is the diameter of one corresponding pulley 31, 31b, 31c of the end-effector 31; and
 iv) Dm is the diameter of one corresponding pulley 30a, 30b, 30c of the handle 30.

The configuration of the mechanical teleoperated device according to the invention allows the operator to easily remove the distal part 10a, comprising at its distal end the end-effector 31, and to replace it with another distal part comprising any type of end-effector such as scissors, scalpels, cutters, needle holders or any other surgical accessories.

Although the transmission system as disclosed in this preferred embodiment comprises cables, its particular configuration is not limited to this embodiment. For example, the present invention may also encompasses other flexible and non-flexible drive elements such as rods, linkages or the like which could be arranged to achieve the same functionality set forth herein.

Moreover, although the transmission system of the mechanical teleoperated device according to the preferred embodiment comprises first, second and third transmission means comprising each three cables to actuate three degrees of freedom of the end-effector when the handle is operated, the scope of the invention also covers configurations with first and second transmission means only such that their respective cables circumvents only joint 19 of the slave unit to allow detachment of the distal part 10a from the proximal part 10b of the slave unit 10. Transmission means in excess of three comprising each a distinct set of cables can also be envisaged to cover embodiments in which the master and slave units comprise each several coaxial joints.

While this invention has been particularly shown and described with references to particular embodiments thereof, it will be understood by those skilled in the art that various changes in form and details may be made therein without departing from the spirit and scope of the invention as defined by the appended claims. For example the scope of the invention includes configurations where at least the first and the third transmission means comprise N cables for the transmission of N degrees-of-freedom of the handle to the end-effector, where N can be for example 2, 4 or 5. In addition, the transmission system disclosed according to the embodiments described herein can be adapted to any teleoperated device which does not necessarily comprise a kinematically equivalent master-slave configuration.

The invention claimed is:

1. A mechanical teleoperated device comprising:
 a handle having a plurality of handle links interconnected by respective handle joints;
 an end effector spaced apart from the handle and having a plurality of end-effector links interconnected by respective end-effector joints;
 a transmission system that kinematically couples the end effector to the handle such that movements of the end effector correspond to movements of the handle, the transmission system comprising:
  a plurality of independently rotatable elements coaxially mounted about a single axis;
  a plurality of driving elements arranged to cause rotation of the plurality of independently rotatable elements responsive to movements of the handle; and
  a plurality of driven elements arranged to cause movement of the end effector links responsive to rotation of the plurality of independently rotatable elements,
 wherein the transmission system is configured for removably coupling the plurality of driving elements to the plurality of driven elements such that each one of the plurality of driven elements is removably coupled to a corresponding one of the plurality of independently rotatable elements.

2. The mechanical teleoperated device of claim 1, wherein a segment of each driven element is removably connected to a corresponding independently rotatable element such that each segment is guided along a path within a plane which is substantially perpendicular to the axis about which the corresponding independently rotatable element is arranged to rotate.

3. The mechanical teleoperated device of claim 2, wherein the path extends along a circular trajectory having a center point coincident with the single axis.

4. The mechanical teleoperated device of claim 1, wherein the single axis coincides with the axis of a joint of the mechanical teleoperated device.

5. The mechanical teleoperated device of claim 1, wherein each driven element is anchored to a mating receptacle pivotally mounted about the single axis, wherein each corresponding independently rotatable element comprises a complementary mating part configured to be removably mounted inside the mating receptacle.

6. The mechanical teleoperated device of claim 5, wherein each mating part is mounted on a support connected to a corresponding independently rotatable element.

7. The mechanical teleoperated device of claim 6, wherein the mating receptacles and corresponding mating parts are housed inside a first housing, the first housing comprising first and second complementary housing parts removably mounted together.

8. The mechanical teleoperated device of claim 7, wherein the mating receptacles are mounted inside the first complementary housing part and wherein the complementary mating parts are mounted inside the second complementary housing part.

9. The mechanical teleoperated device of claim 1, wherein the plurality of independently rotatable elements are arranged into two groups, wherein a first group of independently rotatable elements are coaxially mounted to rotate about a first axis of rotation and a second group of independently rotatable elements are coaxially mounted to rotate about a second axis of rotation.

10. The mechanical teleoperated device of claim 9, wherein each driving element is connected to an independently rotatable element of the first group and to a corresponding independently rotatable element of the second group.

11. The mechanical teleoperated device of claim 10, wherein the second axis is coincident with the axis of a joint of the mechanical teleoperated device.

12. The mechanical teleoperated device of claim 11, wherein the transmission system further comprises links kinematically connected to an actuable element of the handle.

13. The mechanical teleoperated device of claim 12, wherein a segment of each link is anchored to a corresponding rotatable element of the second group.

14. The mechanical teleoperated device of claim 1, wherein the mechanical teleoperated device has a master-slave configuration, comprising a slave unit, having a plurality of slave links interconnected by respective slave joints, and a master unit having a plurality of master links interconnected by respective master joints.

15. The mechanical teleoperated device of claim 14, wherein the kinematic model of plurality of slave links and respective slave joints of the slave unit is identical to the kinematic model of the plurality of master links and respective master joints of the mater unit.

\* \* \* \* \*